(12) United States Patent
Grezaud et al.

(10) Patent No.: US 9,353,320 B2
(45) Date of Patent: May 31, 2016

(54) OPTIMIZED METHOD FOR PRODUCING MIDDLE DISTILLATES FROM A FEEDSTOCK ORIGINATING FROM THE FISCHER-TROPSCH PROCESS CONTAINING A LIMITED QUANTITY OF OXYGENATED COMPOUNDS

(71) Applicants: ENI S.p.A., Rome (IT); IFP Energies nouvelles, Rueil-Malmaison Cedex (FR)

(72) Inventors: Aline Grezaud, Lyons (FR); Jean Philippe Heraud, Saint Pierre de Chandieu (FR); Hugues Dulot, Lyons (FR); Christophe Bouchy, Lyons (FR); Vincenzo Calemma, Milan (IT)

(73) Assignees: IFP Energies Nouvelles, Rueil-Malmaison (FR); ENI S.p.A., Rome (IT)

( * ) Notice: Subject to any disclaimer, the term of this patent is extended or adjusted under 35 U.S.C. 154(b) by 415 days.

(21) Appl. No.: 13/860,850

(22) Filed: Apr. 11, 2013

(65) Prior Publication Data

US 2013/0270154 A1    Oct. 17, 2013

(30) Foreign Application Priority Data

Apr. 12, 2012 (FR) .................................. 12 01075

(51) Int. Cl.
*C10G 65/12* (2006.01)
*C07C 1/04* (2006.01)
(Continued)

(52) U.S. Cl.
CPC ................ *C10G 65/12* (2013.01); *B01J 21/12* (2013.01); *B01J 23/42* (2013.01); *B01J 23/44* (2013.01);
(Continued)

(58) Field of Classification Search
CPC .............. C10G 3/00; C10G 3/42; C10G 3/44; C10G 3/45; C10G 3/46; C10G 65/02; C10G 65/12; C10G 45/00; C10G 45/02; C07C 27/06; C07C 27/08
See application file for complete search history.

(56) References Cited

U.S. PATENT DOCUMENTS 6,583,186 B2   6/2003  Moore, Jr.
6,900,366 B2   5/2005  Rosenbaum et al.
(Continued)

FOREIGN PATENT DOCUMENTS

EP            0297949    * 10/1990 ............. B01J 27/188

OTHER PUBLICATIONS

Satterfield, C.N. (1980). Heterogenous Catalysis in Practice, McGraw-Hill, 416 pgs (Office action p. 79).*

(Continued)

*Primary Examiner* — Brian McCaig
(74) *Attorney, Agent, or Firm* — Millen White Zelano and Branigan, PC; John Sopp; Anthony Zelano

(57) ABSTRACT

A method for producing middle distillates from a feedstock produced by Fischer-Tropsch synthesis and containing oxygenated compounds, including:
a) a step of bringing the feedstock into contact with a hydrotreating catalyst allowing the methanation of the CO and $CO_2$ contained in the feedstock or originating from the decomposition of the oxygenated compounds present in the feedstock,
b) a step of hydroisomerization/hydrocracking of at least a part of the liquid and gaseous effluent originating from step a), in the presence of a hydroisomerization/hydrocracking catalyst,
c) a step of gas/liquid separation of the effluent originating from step b) into a gaseous fraction comprising predominantly hydrogen and a hydroisomerized/hydrocracked liquid fraction,
d) a step of fractionation of the liquid fraction separated in step c) to obtain at least one fraction of middle distillate, in which the hydrogen in step a) is obtained from the gaseous fraction separated in step c).

13 Claims, 1 Drawing Sheet

(51) Int. Cl.
- C07C 1/12 (2006.01)
- B01J 21/12 (2006.01)
- B01J 23/42 (2006.01)
- B01J 23/44 (2006.01)
- B01J 23/75 (2006.01)
- B01J 23/755 (2006.01)
- B01J 23/882 (2006.01)
- B01J 23/883 (2006.01)
- B01J 23/888 (2006.01)
- B01J 35/00 (2006.01)
- B01J 35/10 (2006.01)
- B01J 37/00 (2006.01)
- B01J 37/02 (2006.01)
- C10G 65/02 (2006.01)
- C07C 27/06 (2006.01)
- C07C 27/08 (2006.01)
- C10G 45/00 (2006.01)
- C10G 45/02 (2006.01)

(52) U.S. Cl.
CPC ............ *B01J 23/75* (2013.01); *B01J 23/755* (2013.01); *B01J 23/882* (2013.01); *B01J 23/883* (2013.01); *B01J 23/888* (2013.01); *B01J 23/8885* (2013.01); *B01J 35/0026* (2013.01); *B01J 35/0066* (2013.01); *B01J 35/1019* (2013.01); *B01J 35/1042* (2013.01); *B01J 35/1061* (2013.01); *B01J 37/0009* (2013.01); *B01J 37/0201* (2013.01); *C07C 1/0495* (2013.01); *C07C 1/12* (2013.01); *Y02P 20/52* (2015.11)

(56) References Cited

U.S. PATENT DOCUMENTS

| | | |
|---|---|---|
| 8,137,531 B2 | 3/2012 | Farshid et al. |
| 2003/0019788 A1* | 1/2003 | Benazzi et al. ............... 208/57 |
| 2009/0018374 A1 | 1/2009 | Bijlsma et al. |
| 2011/0000819 A1* | 1/2011 | Keusenkothen ............... 208/89 |
| 2012/0029095 A1 | 2/2012 | Junaedi et al. |

OTHER PUBLICATIONS

Aksoylu, A.E. et al. (1998). Applied Catalysis A: General, 168,385-397.*

Zhao, L. et al. (2012). The Journal of Physical Chemistry A, 116, 9238-9244.*

French Search Report for FR 1201075 (Oct. 30, 2012).

A. de Klerk, "Hydroprocessing Peculiarities of Fischer-Tropsch Syncrude", Catalysis Today, vol. 130 (2008) pp. 439-445.

K. P. Brooks et al., "Methanation of Carbon Dioxide by Hydrogen Reduction Using the Sabatier Process in Microchannel Reactors", Chemical Engineering Science, vol. 62 (2007) pp. 1161-1170.

C. Bouchy et al., "Fischer-Tropsch Waxes Upgrading via Hydrocracking and Selective Hydroisomerization", Oil & Gas Science and Technology, vol. 64, No. 1 (2009) pp. 91-112.

* cited by examiner

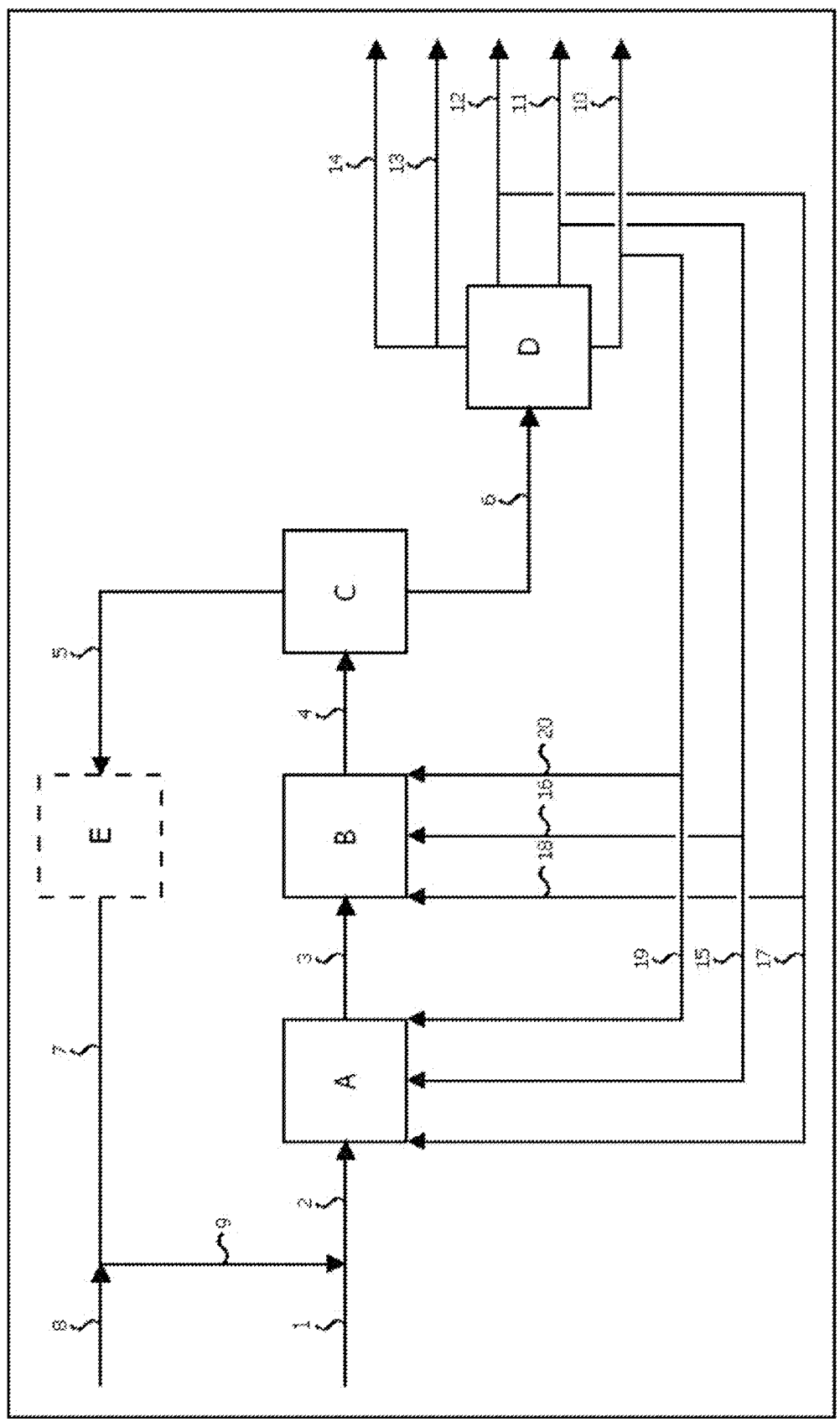

OPTIMIZED METHOD FOR PRODUCING MIDDLE DISTILLATES FROM A FEEDSTOCK ORIGINATING FROM THE FISCHER-TROPSCH PROCESS CONTAINING A LIMITED QUANTITY OF OXYGENATED COMPOUNDS

The present invention relates to a method for producing middle distillates from a feedstock produced by Fischer-Tropsch synthesis and containing oxygenated compounds.

PRIOR ART

In the low-temperature Fischer-Tropsch process, synthesis gas ($CO+H_2$) is converted catalytically into water and into a hydrocarbon effluent comprising unsaturated compounds, oxygenated compounds and essentially linear paraffinic hydrocarbons in gaseous, liquid or solid form. Said effluent thus produced is generally free from heteroatomic impurities such as, for example, sulphur, nitrogen or metals. Said paraffinic feedstock contains hardly any or no aromatics, naphthenes and more generally ring compounds.

The liquid hydrocarbons produced by Fischer-Tropsch synthesis cannot be incorporated directly in the fuel pools or used as lubricants. As an example, the melting point of a paraffin with 20 carbon atoms and having a boiling point of 340° C. is about 37° C., which makes its direct incorporation in the gas oil cut impossible in view of the required specification of −15° C. Moreover, these liquid hydrocarbons are composed predominantly of paraffins, but also contain olefins and oxygenated compounds. These liquid hydrocarbons thus need to be converted into higher-grade products, such as for example kerosene and gas oil, which are obtained, for example, after catalytic reactions of hydroisomerization and hydrocracking.

All the catalysts currently used in hydroisomerization/hydrocracking are of the bifunctional type, combining an acid function with a hydrogenating function. The acid function is supplied by supports with large surface areas (generally 150 to 800 $m^2 \cdot g^{-1}$) displaying Brønsted acidity, such as halogenated aluminas (in particular chlorinated or fluorinated), phosphorus-containing aluminas, combinations of oxides of boron and aluminium, silica-aluminas or zeolites. The hydrogenating function is supplied either by one or more metals of group VIII of the periodic table, such as iron, cobalt, nickel, ruthenium, rhodium, palladium, osmium, iridium and platinum, or by a combination of at least one group VI metal such as chromium, molybdenum and tungsten and at least one group VIII metal.

The balance between the two acid and hydrogenating functions is one of the parameters governing the activity and selectivity of the catalyst. A weak acid function and a strong hydrogenating function produce catalysts with low activity and selectivity for isomerization, whereas a strong acid function and a weak hydrogenating function produce catalysts that are very active and selective for cracking. A third possibility is to use a strong acid function and a strong hydrogenating function in order to obtain a catalyst that is very active, but also very selective for isomerization. It is therefore possible, by judicious selection of each of the functions, to adjust the activity/selectivity combination of the catalyst.

It is known, in the area of hydrocracking and hydroisomerization of paraffinic feedstocks originating from Fischer-Tropsch synthesis, that the presence of oxygenated compounds in the paraffinic feedstocks originating from Fischer-Tropsch synthesis can affect the balance between the acid and hydrogenating functions of the hydrocracking/hydroisomerization catalyst located downstream and therefore affect its catalytic properties. The oxygenated compounds present in said paraffinic feedstocks are generally oxides of carbon such as carbon monoxide and carbon dioxide (CO and $CO_2$), water or else alcohols and/or carboxylic acids, esters and ketones.

For example, D. Leckel in D. Leckel, Energy & Fuels 2005, 19, 1795-1803 reports a study showing that removal of the oxygenated compounds by hydrotreating a feedstock originating from Fischer-Tropsch synthesis makes it possible to improve the activity of the downstream hydrocracking catalyst by about fifteen degrees Celsius, but impairs the selectivity of the catalyst for production of middle distillates. Now, during the step of hydrotreating of the paraffinic feedstock, the hydrocarbon compounds possessing at least one double bond are hydrogenated, whereas the oxygenated compounds, such as the alcohols and/or carboxylic acids, esters and ketones, are decomposed. This hydrotreating step has low conversion. The decomposition products in this step are paraffins obtained from the olefinic compounds and water, CO and $CO_2$ obtained from the decomposition of the alcohols and/or carboxylic acids, esters and ketones. Thus, as the cycles proceed, CO and $CO_2$ become more and more concentrated in the recycled hydrogen, and consequently in the effluent leaving the hydrotreating unit, and greatly inhibit the catalysts used downstream, in particular the hydroisomerization/hydrocracking catalyst.

Several solutions have been proposed in the prior art for limiting the content of oxygenated compounds present in the hydrogen entering the hydroisomerization/hydrocracking units.

Thus, patent EP 0 583 836 B2 teaches the use of a method for preparing gas oil implementing: a) a step of hydrotreating the hydrocarbon feedstock originating from Fischer-Tropsch synthesis in order to saturate the olefins in the feedstock and decompose the oxygenated compounds present, followed by a step (b) of removal of the $C_4^-$ fraction from the hydrotreated feedstock and a step c) of hydrocracking of at least part of the hydrocarbon effluent originating from step b). It is taught that the implementation of steps (a) and (b) makes it possible to prolong the life of the hydroconversion catalyst in step (c), as well as to improve the selectivity of the catalyst for production of gas oil.

U.S. Pat. No. 6,709,569 B2 describes a specific method for production of hydrocarbon effluent of the middle distillate type from a feedstock originating from a Fischer-Tropsch synthesis process, said feedstock being fractionated into a light fraction and a heavy fraction, so that said light fraction undergoes a step of removal of oxides of carbon dissolved in said light fraction ($C_3$-$C_{20}$ fraction) by stripping, distillation or fractionation before undergoing a step of hydrotreating and hydrocracking in a mixture with said heavy fraction.

The applicant, in his previous research, discovered a method for producing middle distillates from a paraffinic feedstock produced by Fischer-Tropsch synthesis comprising at least: a) a step of hydrotreating said feedstock in the presence of hydrogen and a hydrotreating catalyst, b) a step of separation of at least a part of the effluent originating from step a) into at least one light fraction, at least one liquid hydrocarbon effluent and at least one liquid effluent comprising water, c) a step of hydroisomerization/hydrocracking of at least a part of the liquid hydrocarbon effluent originating from step b), in the presence of a hydroisomerization/hydrocracking catalyst and of a hydrogen stream that has undergone a purification step in the case when the content of atomic oxygen in said hydrogen stream is greater than 500 ppm by volume, d) a step of fractionation of the effluent from step c) to obtain at least one fraction of middle distillates.

Therefore there is still a need to provide methods that are more economical and more powerful for treating a feedstock produced by Fischer-Tropsch synthesis in which the downstream hydroisomerization/hydrocracking step operates in the presence of a feedstock comprising a limited content of oxygenated compounds, in particular of $H_2O$, CO and $CO_2$. Such a limitation makes it possible to improve the performance of the hydroisomerization/hydrocracking catalyst, but also the low-temperature properties of the middle distillate cut and in particular of the gas oil cut produced by the method, while maintaining a good cetane number.

The applicant has found a method for producing middle distillates utilizing a feedstock produced by Fischer-Tropsch synthesis which undergoes: a) a step of bringing the feedstock into contact with at least one hydrotreating catalyst for methanation of the CO and $CO_2$ contained in the feedstock or from decomposition of the oxygenated compounds present in the feedstock under particular operating conditions, b) a step of hydroisomerization/hydrocracking of at least part of the gaseous and liquid effluent originating from step a) in the presence of a hydroisomerization/hydrocracking catalyst, c) a step of gas/liquid separation of the effluent originating from step b) into a gaseous fraction comprising predominantly hydrogen and a hydroisomerized/hydrocracked liquid fraction, d) a step of fractionation of the liquid fraction separated in step c) to obtain at least one fraction of middle distillates, in which method the hydrogen in step a) is obtained from the gaseous fraction separated in step c).

SUBJECT MATTER OF THE INVENTION

The present invention relates to a method for producing middle distillates from a feedstock produced by Fischer-Tropsch synthesis and containing oxygenated compounds, said method comprising at least:
a) a step of bringing the feedstock into contact with a hydrotreating catalyst allowing the methanation of the CO and $CO_2$ contained in the feedstock or originating from the decomposition of the oxygenated compounds present in the feedstock, at a temperature comprised between 250 and 450° C., at a pressure comprised between 0.5 and 15 MPa, the hydrogen necessary for the reaction of hydrotreating and of methanation being introduced at a flow rate such that the hydrogen/feedstock volume ratio is comprised between 100 and 3000 normal litres per litre, and at an hourly space velocity comprised between 0.1 and 40 $h^{-1}$,
b) a step of hydroisomerization/hydrocracking of at least a part of the liquid and gaseous effluent originating from step a), in the presence of a hydroisomerization/hydrocracking catalyst,
c) a step of gas/liquid separation of the effluent originating from step b) into a gaseous fraction comprising predominantly hydrogen and a hydroisomerized/hydrocracked liquid fraction,
d) a step of fractionation of the liquid fraction separated in step c) to obtain at least one fraction of middle distillate,
in which the hydrogen in step a) is obtained from the gaseous fraction separated in step c).

Hereinafter, by "oxygenated molecules, products or compounds" is meant any compound containing at least one oxygen atom such as the alcohols and/or carboxylic acids, esters, ketones etc. The decomposition products of said oxygenated compounds are understood as substantially comprising CO, $CO_2$ and $H_2O$.

SUMMARY OF THE INVENTION

The present invention relates to a method for producing middle distillates from a feedstock produced by Fischer-Tropsch synthesis and containing oxygenated compounds, said method comprising at least:
a) a step of bringing the feedstock into contact with a hydrotreating catalyst allowing the methanation of the CO and $CO_2$ contained in the feedstock or originating from the decomposition of the oxygenated compounds present in the feedstock, at a temperature comprised between 250 and 450° C., at a pressure comprised between 0.5 and 15 MPa, the hydrogen necessary for the reaction of hydrotreating and of methanation being introduced at a flow rate such that the hydrogen/feedstock volume ratio is between 100 and 3000 normal litres per litre, and at an hourly space velocity comprised between 0.1 and 40 $h^{-1}$,
b) a step of hydroisomerization/hydrocracking of at least a part of the liquid and gaseous effluent originating from step a), in the presence of a hydroisomerization/hydrocracking catalyst,
c) a step of gas/liquid separation of the effluent originating from step b) into a gaseous fraction comprising predominantly hydrogen and a hydroisomerized/hydrocracked liquid fraction,
d) a step of fractionation of the liquid fraction separated in step c) to obtain at least one fraction of middle distillate,
in which the hydrogen in step a) is obtained from the gaseous fraction separated in step c).

Advantageously, the feedstock for the method of the invention is a feedstock produced by Fischer-Tropsch synthesis comprising an n-paraffins content greater than 60% by weight relative to the total weight of said feedstock, a content of oxygenated compounds less than 10% by weight, a content of unsaturated compounds less than 20% by weight and a content of iso-paraffins less than 10% by weight relative to the total weight of said feedstock.

Advantageously according to the invention, the catalyst used in step a) comprises at least one hydrogenating-dehydrogenating metal selected from the group comprising the metals of group VIB and of group VIII of the periodic table on a support.

In a preferred embodiment according to the invention, the catalyst used in step a) comprises at least one group VIII non-noble metal selected from nickel and cobalt in combination with at least one group VIB metal selected from molybdenum and tungsten, used alone or in a mixture.

Advantageously, the catalyst support used in step a) is an alumina-based support. Preferably, the catalyst support used in step a) is an alumina-based support containing a group VIII metal selected from nickel or cobalt.

Advantageously according to the invention, the catalyst used in step a) is used in reduced form.

Advantageously according to the invention, step b) is implemented on all of the effluent originating from step a).

Step b) according to the invention is advantageously carried out at a temperature comprised between 250 and 450° C., at a pressure comprised between 0.2 and 15 MPa, at a space velocity comprised between 0.1 $h^{-1}$ and 10 $h^{-1}$, and at a hydrogen rate between 100 and 2000 normal litres of hydrogen per litre of feedstock per hour.

Advantageously according to the invention, the gaseous fraction separated in step c) is subjected to a step e) of removal of water before being recycled to step a) of hydrotreating. Preferably said gaseous fraction separated in step c) is recycled to step a) of hydrotreating at the same time as fresh hydrogen is supplied.

LIST OF FIGURES

FIG. 1 shows a general diagram of the method according to the invention, presented here as non-limitative.

DETAILED DESCRIPTION OF THE INVENTION

FEEDSTOCK

According to the invention, the feedstock used is a feedstock produced by Fischer-Tropsch synthesis according to methods known to a person skilled in the art. The feedstock according to the invention can comprise oxygenated compounds and essentially linear hydrocarbons in gaseous, liquid or solid form. The synthesis gas ($CO+H_2$) used in Fischer-Tropsch synthesis giving rise to the feedstock according to the invention is advantageously produced from natural gas, charcoal, biomass or from any source of hydrocarbon compounds or from a mixture of these sources.

Preferably, the feedstock according to the invention comprises predominantly n-paraffins. Said feedstock can advantageously comprise a content of n-paraffins greater than 60% by weight relative to the total weight of said feedstock, a content of oxygenated compounds preferably less than 10% by weight, a content of unsaturated compounds, i.e. preferably of olefinic products, preferably less than 20% by weight and a content of iso-paraffins preferably less than 10% by weight relative to the total weight of said feedstock. More preferably, said feedstock comprises an n-paraffins content greater than 70% by weight, and even more preferably greater than 80% by weight relative to the total weight of said feedstock.

Advantageously, said feedstock according to the invention is free from heteroatomic impurities such as, for example, sulphur, nitrogen or metals.

Step a) of Hydrotreating

According to step a) of the method according to the invention, the feedstock according to the invention is brought into contact with at least one hydrotreating catalyst for methanation of the CO and $CO_2$ contained in the feedstock in the presence of hydrogen obtained from the gaseous fraction separated in step c). The catalyst implemented in step a), in addition to the hydrotreating reaction, is active for decomposition of the oxygenated compounds and in methanation of CO and $CO_2$ to methane, i.e. it makes it possible to catalyse the reaction of methanation of the CO and $CO_2$ contained in the feedstock or originating from the decomposition of the oxygenated compounds present in the feedstock, under the operating conditions of said step a).

Said catalyst is generally a supported catalyst advantageously comprising at least one hydrogenating-dehydrogenating metal selected from the group comprising the metals of group VIB and of group VIII of the periodic table. Preferably, the catalyst implemented in step a) comprises at least one group VIII non-noble metal selected from nickel and cobalt in combination with at least one group VIB metal selected from molybdenum and tungsten, used alone or in a mixture. Preferably, the catalyst implemented in step a) is used in reduced form.

Advantageously, the content of group VIB metal in the catalyst used in step a) is comprised, in oxide equivalent, between 5 and 40% by weight relative to the finished catalyst, preferably between 5 and 20% by weight, and the content of group VIII metal in the catalyst is comprised, in oxide equivalent, between 5 and 40% by weight relative to the finished catalyst, preferably between 5 and 20% by weight.

The metallic function is advantageously introduced onto the catalyst by any method known by a person skilled in the art, for example co-mixing, dry impregnation or exchange impregnation. The metallic function is deposited on a mineral support, preferably of low acidity. The support of the catalyst used in step a) is preferably an alumina-based support. Advantageously, the support is constituted by an alumina containing a group VIII metal selected from nickel or cobalt, preferably nickel.

Advantageously according to the invention, the catalyst used in step a) has:
- a BET specific surface area from 100 to 300 $m^2/g$, preferably comprised between 100 $m^2/g$ and 250 $m^2/g$,
- a mean mesopore diameter comprised between 6 and 20 nm, preferably comprised between 6 nm and 18 nm, very preferably between 6 nm and 16 nm, more preferably between 10 nm and 16 nm,
- a pore volume of the pores the diameter of which is comprised between the average diameter as defined above reduced by 3 nm and the average diameter as defined above increased by 3 nm is greater than 20% of the total pore volume, preferably comprised between 25% and 90% of the total pore volume, and very preferably comprised between 30% and 70% of the total pore volume,
- a total pore volume comprised between 0.1 and 1 ml/g, preferably between 0.2 and 0.8 ml/g, and very preferably between 0.3 and 0.6 ml/g.

According to the invention, the average mesopore diameter is defined as being the diameter corresponding to the cancellation of the curve derived from the mercury intrusion volume obtained from the mercury porosity curve for pore diameters comprised between 3.7 and 50 nm. The average mesopore diameter of the catalyst used in step a) is advantageously measured from the pore distribution profile obtained by means of a mercury porosimeter.

The catalyst according to the invention can be prepared by means of any technique known by a person skilled in the art, and in particular by impregnation of the elements of groups VIII and VIB on the support selected. This impregnation can for example be carried out according to the method known by a person skilled in the art by the term dry impregnation, in which exactly the quantity of desired elements is introduced in the form of salts soluble in the solvent selected, for example demineralized water, so as to fill the porosity of the support as precisely as possible. The support thus filled with the solution is preferably dried. The preferred support is alumina, which can be prepared from any type of precursors and forming tools known by a person skilled in the art.

After introducing the elements of groups VIII and VIB, and optionally forming the catalyst, the latter is subjected to an activation treatment. This treatment in particular has the aim of converting the molecular precursors of the elements to the oxide phase. In this case it is an oxidizing treatment, but a simple drying of the catalyst can also be carried out. In the case of an oxidizing treatment, also called calcination, the latter is generally implemented under air or under diluted oxygen, and the treatment temperature is generally comprised between 200° C. and 550° C., preferably between 300° C. and 500° C. Salts of metals of groups VIB and VIII usable in the method for preparing the catalyst are for example cobalt nitrate, nickel nitrate, ammonium heptamolybdate or ammonium metatungstate. Any other salt known by a person skilled in the art having sufficient solubility and that can decompose during the activation treatment can also be used. After calcination, the metals deposited on the support are in the form of oxide. In the case of nickel and molybdenum, the metals are found principally in the form of $MoO_3$ and NiO. Before being brought into contact with the feedstock to be treated, the catalysts undergo a reduction step.

According to the invention, the catalyst used in step a) is advantageously reduced beforehand under a stream of hydrogen, pure or in a mixture, preferably of pure hydrogen at hydrogen flow rates comprised between 100 and 2000 normal litres per hour per litre of catalyst, preferably between 300 and 1500 normal litres per hour per litre of catalyst, preferably at a temperature comprised between 100 and 500° C., preferably comprised between 150 and 450° C., for a time comprised between 1 and 100 hours, preferably between 1 and 60 hours.

Step a) of hydrotreating and methanation of the method of the invention is advantageously carried out at a temperature comprised between 250 and 450° C., preferably between 280 and 450° C., more preferably between 320 and 420° C., at a pressure comprised between 0.5 and 15 MPa, preferably between 1 and 10 MPa, more preferably between 1 and 9 MPa, more preferably between 4 and 9 MPa, very preferably between 4 and 8 MPa with a hydrogen flow rate such that the hydrogen/feedstock volume ratio is between 100 and 3000 normal litres per litre, preferably between 100 and 2000 normal litres per litre, more preferably between 150 and 2000 normal litres per litre, very preferably between 300 and 1500 normal litres per litre and at an hourly space velocity comprised between 0.1 and 40 $h^{-1}$, preferably between 0.2 and 30 $h^{-1}$, very preferably between 0.2 and 20 $h^{-1}$, more preferably between 0.2 and 10 $h^{-1}$, even more preferably between 0.2 and 5 h'.

In one variant, step a) of hydrotreating and methanation of the method of the invention is advantageously carried out at a temperature comprised between 250 and 400° C., preferably between 280 and 400° C., very preferably between 280 and 380° C., more preferably between 320 and 380° C.

At the end of step a) of hydrotreating according to the invention, the residual contents in the whole gaseous and liquid effluent at the outlet of said step a) are advantageously less than 1% by weight of olefins relative to the total weight of the effluent, advantageously less than 0.01% by weight of oxygenated compounds in the liquid phase and advantageously less than 0.02% by volume of CO and $CO_2$ in the gas phase, preferably less than 500 ppm by volume of CO and $CO_2$, very preferably less than 250 ppm by volume of CO and $CO_2$, even more preferably less than 50 ppm by volume of CO and $CO_2$, and very preferably less than 10 ppm by volume of CO and $CO_2$ in the gas phase.

Advantages of the Invention

The use of the catalyst described above in step a) of hydrotreating has the following advantages:
- it reduces the content of olefinic compounds,
- it converts, essentially to CO and $CO_2$, the oxygenated compounds such as the alcohols and/or carboxylic acids, esters and ketones present in the feedstock according to the invention, to paraffin and CO, $CO_2$ and $H_2O$
- but also, simultaneously, it reduces the quantity of said compounds CO and $CO_2$ produced during the hydrotreating reaction and those brought in by the hydrogen obtained from the gaseous fraction separated in step c), by methanation.

Step a) according to the invention also offers the economic advantage of doing away with the need to employ, after hydrotreating and before the hydroisomerization/hydrocracking step, a unit for fractionation and/or removal of the oxygenated compounds for example by separation of the liquid phase from the gas phase. In fact, the hydroisomerization/hydrocracking step is implemented at least partly on the liquid and gaseous effluent. Moreover, said step a) makes it possible to avoid the need to use a separate unit for removing the compounds CO and $CO_2$ contained in the hydrogen obtained from the gaseous fraction separated in step c).

Step b) of hydroisomerization/hydrocracking

According to step b) of hydroisomerization/hydrocracking, at least a part, preferably all of the liquid and gaseous effluent originating from step a) of hydrotreating is brought into contact with a hydroisomerization/hydrocracking catalyst.

Advantageously, step b) of hydroisomerization/hydrocracking is carried out at a temperature comprised between 250° C. and 450° C., more preferably between 280 and 450° C., and even more preferably between 320 and 420° C., at a pressure comprised between 0.2 and 15 MPa, preferably between 0.5 and 10 MPa, more preferably between 1 and 9 MPa, at a space velocity defined as being the ratio of the flow rate of feedstock at ambient temperature and pressure to the volume of catalyst, comprised between 0.1 $h^{-1}$ and 10 $h^{-1}$, preferably between 0.2 and 7 $h^{-1}$, more preferably between 0.5 and 5 $h^{-1}$, at a hydrogen rate comprised between 100 and 2000 normal litres of hydrogen per litre of feedstock per hour and preferably between 150 and 1500 normal litres of hydrogen per litre of feedstock and more preferably between 300 and 1500 normal litres of hydrogen per litre of feedstock.

Step b) of hydroisomerization/hydrocracking of the method according to the invention is advantageously carried out under conditions such that conversion of the products with boiling points above or equal to 370° C. to products having boiling points below 370° C. is greater than 30% by weight, and even more preferably at least 40% by weight, preferably greater than 50% by weight, so as to obtain middle distillates (gas oil and kerosene).

The conversion is defined as:

Conversion of the 370° C.+ to 370° C. products=[(% by weight of the 370° C.$^-_{effluent}$)−(% by weight of the 370° C.$^-_{feedstock}$)]/[100−(% by weight of the 370° C.$^-_{feedstock}$)], with: -% by weight of the 370° C.$^-_{effluent}$=fraction by weight of compounds having boiling points below 370° C. in the effluents, −% by weight of the 370° C.$^-_{feedstock}$=fraction by weight of compounds having boiling points below 370° C. in the hydroisomerization/hydrocracking feedstock.

According to the method of the invention, the hydroisomerization/hydrocracking catalyst used in step b) advantageously comprises at least one hydrogenating-dehydrogenating metal selected from the group comprising the metals of group VIB and of group VIII of the periodic table and at least one solid that is a Brønsted acid, i.e. a solid that can release one or more protons, and optionally a binder. Preferably, said hydroisomerization/hydrocracking catalyst comprises either at least one group VIII noble metal selected from platinum and palladium, used alone or in a mixture, active in their reduced form, or at least one group VIII base metal selected from nickel and cobalt in combination with at least one group VIB metal selected from molybdenum and tungsten, used alone or in a mixture, and preferably used in their sulphided form.

In the case when said hydroisomerization/hydrocracking catalyst comprises at least one group VIII noble metal, the noble metal content of said catalyst is advantageously between 0.01 and 5% by weight relative to the finished catalyst, preferably between 0.05 and 4% by weight and very preferably between 0.10 and 2% by weight.

In the case when said hydroisomerization/hydrocracking catalyst comprises at least one group VIB metal in combination with at least one group VIII non-noble metal selected from nickel and cobalt, the content of group VIB metal of said catalyst is advantageously comprised in oxide equivalent between 5 and 40% by weight relative to the finished catalyst, preferably between 10 and 35% by weight and the content of group VIII metal in said catalyst is advantageously comprised in oxide equivalent between 0.5 and 10% by weight relative to the finished catalyst, preferably between 1 and 8% by weight and very preferably between 1.5 and 6% by weight.

The metallic function is advantageously introduced onto the catalyst by any method known to a person skilled in the art, for example co-mixing, dry impregnation or exchange impregnation.

Advantageously, the solid that is a Brønsted acid consists of silica-alumina or zeolite Y.

Optionally, a binder can also be used during the step of forming the support. It is preferable to use a binder when the zeolite is used. Said binder is advantageously selected from silica ($SiO_2$), alumina ($Al_2O_3$), clays, titanium dioxide ($TiO_2$), boron oxide ($B_2O_3$) and zirconia ($ZrO_2$) used alone or in a mixture. Preferably, said binder is selected from silica and alumina and even more preferably said binder is alumina in all its forms known to a person skilled in the art, such as gamma alumina for example.

A preferred hydroisomerization/hydrocracking catalyst according to the invention advantageously comprises at least one noble metal, said noble metal being platinum and a solid Brønsted acid of the silica-alumina type, without any binder. The silica content of the silica-alumina, expressed as percentage by weight, is generally comprised between 1 and 95%, advantageously between 5 and 95% and preferably between 10 and 80% and even more preferably between 20 and 70% and between 22 and 45%. This silica content is measured accurately by means of X-ray fluorescence.

Several preferred catalysts used in step b) of hydroisomerization/hydrocracking of the method according to the invention are described below.

A preferred hydroisomerization/hydrocracking catalyst used in the method according to the invention comprises a particular silica-alumina. Preferably said catalyst comprises 0.05 to 10% by weight, preferably between 0.1 and 5% by weight of at least one group VIII noble metal, preferably selected from platinum and palladium (preferably platinum) deposited on a silica-alumina support, without any binder, containing a quantity of silica ($SiO_2$) between 1 and 95%, expressed as percentage by weight, preferably between 5 and 95%, preferably between 10 and 80% and very preferably between 20 and 70% and even more preferably between 22 and 45%, said catalyst having:
- a BET specific surface area from 100 to 500 m$^2$/g, preferably between 200 m$^2$/g and 450 m$^2$/g, and very preferably between 250 m$^2$/g and 450 m$^2$/g,
- a mean mesopore diameter between 3 and 12 nm, preferably between 3 nm and 11 nm and very preferably between 4 nm and 10.5 nm,
- a pore volume of the pores the diameter of which is comprised between the average diameter as defined above reduced by 3 nm and the average diameter of which as defined above increased by 3 nm is greater than 40% of the total pore volume, preferably between 50% and 90% of the total pore volume and very preferably between 50% and 70% of the total pore volume,
- a total pore volume comprised between 0.4 and 1.2 ml/g, preferably between 0.5 and 1.0 ml/g and very preferably between 0.5 and 0.9 ml/g,
- a content of alkali or alkaline-earth compounds less than 300 ppm by weight and preferably less than 200 ppm by weight.

The average mesopore diameter is defined as being the diameter corresponding to the cancellation of the curve derived from the mercury intrusion volume obtained from the mercury porosity curve for pore diameters comprised between 2 and 50 nm. The average mesopore diameter of the catalyst is advantageously measured from the pore distribution profile obtained by means of a mercury porosimeter.

Preferably, the dispersion of the metal of said preferred catalyst is advantageously comprised between 20% and 100%, preferably between 30% and 100% and very preferably between 40 and 100%. The dispersion, representing the fraction of metal available to the reagent relative to the total quantity of metal in the catalyst, is advantageously measured, for example, by $H_2/O_2$ titration or by transmission electron microscopy.

Preferably, the distribution coefficient of the noble metal of said preferred catalyst is greater than 0.1, preferably greater than 0.2 and very preferably greater than 0.4. The distribution of the noble metal represents the distribution of the metal within the grain of the catalyst, it being possible for the metal to be dispersed well or poorly. Thus, it is possible to obtain platinum that is poorly distributed (for example detected in a ring the thickness of which is clearly less than the radius of the grain), but well dispersed, i.e. all the platinum atoms, located in the ring, will be accessible to the reagents. The distribution coefficient of the noble metal can be measured by a Castaing microprobe.

The noble metal salt is advantageously introduced by one of the usual methods used for depositing metal on the surface of a solid. One of the preferred methods is dry impregnation, which consists of introducing the metal salt in a volume of solution that is equal to the pore volume of the solid mass to be impregnated. Before the reduction operation, the catalyst can advantageously undergo calcination, for example treatment under dry air at a temperature from 300 to 750° C. and preferably at a temperature equal to 520° C., for 0.25 to 10 hours and preferably for 2 hours.

Another preferred hydroisomerization/hydrocracking catalyst used in the method according to the invention comprises at least one hydrogenating-dehydrogenating element selected from the group comprising the elements of group VIB and of group VIII of the periodic table, from 0.01 to 5.5% by weight of oxide of a doping element selected from phosphorus, boron and silicon and a non-zeolitic support based on silica-alumina containing a quantity greater than 5% by weight and less than or equal to 95% by weight of silica ($SiO_2$), said catalyst having the following characteristics:
- a mean mesopore diameter, measured by mercury porosimetry, comprised between 2 and 14 nm,
- a total pore volume, measured by mercury porosimetry, comprised between 0.1 ml/g and 0.5 ml/g,
- a total pore volume, measured by nitrogen porosimetry, comprised between 0.1 ml/g and 0.5 ml/g,
- a BET specific surface area comprised between 100 and 550 m$^2$/g,
- a pore volume, measured by mercury porosimetry, comprised in the pores with a diameter greater than 14 nm, less than 0.1 ml/g,
- a pore volume, measured by mercury porosimetry, comprised in the pores with a diameter greater than 16 nm, less than 0.1 ml/g,
- a pore volume, measured by mercury porosimetry, comprised in the pores with a diameter greater than 20 nm, less than 0.1 ml/g,
- a pore volume, measured by mercury porosimetry, comprised in the pores with a diameter greater than 50 nm, less than 0.1 ml/g, an X-ray diffraction diagram that contains at least the principal lines characteristic of at least one of the transition aluminas included in the group comprising the alpha, rho, chi, eta, gamma, kappa, theta and delta aluminas, a tapped bulk density greater than 0.7 g/ml.

Another preferred hydroisomerization/hydrocracking catalyst used in the method according to the invention comprises (and preferably essentially consists of) 0.05 to 10% by weight and preferably 0.1 to 5% by weight of at least one group VIII noble metal, preferably selected from platinum and palladium and preferably said noble metal being platinum, deposited on a silica-alumina support, without any binder, containing a quantity of silica ($SiO_2$) comprised between 1 and 95%, expressed as percentage by weight, preferably between 5 and 95%, preferably between 10 and 80% and very preferably between 20 and 70% and even more preferably between 22 and 45%, said catalyst having:

- a BET specific surface area from 150 to 600 $m^2/g$ and preferably between 200 $m^2/g$ and 600 $m^2/g$,
- a mean mesopore diameter between 3 and 12 nm, preferably between 3 nm and 11 nm and very preferably between 4 nm and 10.5 nm,
- a pore volume of the pores the diameter of which is comprised between the average diameter as defined above reduced by 3 nm and the average diameter as defined above increased by 3 nm is greater than 60% of the total pore volume, preferably greater than 70% of the total pore volume and very preferably greater than 80% of the total pore volume,
- a total pore volume less than 1 ml/g, preferably between 0.1 and 0.9 ml/g and very preferably between 0.2 and 0.8 ml/g,
- a content of alkali or alkaline-earth compounds less than 300 ppm by weight and preferably less than 200 ppm by weight.

Preferably, the dispersion of said preferred catalyst used in step b) of the method according to the invention is advantageously between 20% and 100%, preferably between 30% and 100% and very preferably between 40% and 100%.

Preferably, the distribution coefficient of the noble metal of said preferred catalyst used in step b) of the method according to the invention is greater than 0.1, preferably greater than 0.2 and very preferably greater than 0.4. This distribution coefficient is measured by Castaing microprobe.

Step c) of gas/liquid separation of the effluent originating from step b)

According to the method of the invention, the hydroisomerized/hydrocracked effluent originating from step b) undergoes a step c) of gas/liquid separation into a gaseous fraction comprising predominantly hydrogen and a hydroisomerized/hydrocracked liquid fraction. Said separation step c) is advantageously carried out by any method and technique known to a person skilled in the art. Preferably, said step c) is advantageously carried out by distillation, stripping and/or flash, combined with drying, passing over a desiccator or drying agent, or a trapping sieve (of the alumina type), solvent extraction, decanting or a combination of at least two of these methods. Advantageously, said step c) comprises a flash operation, followed by a decanting operation.

According to the invention, the gaseous fraction originating from step c) of gas/liquid separation advantageously comprises between 20 and 99% by volume of hydrogen, preferably between 40 and 99% by volume of hydrogen, more preferably between 50 and 99% by volume of hydrogen, even more preferably between 80 and 99% by volume of hydrogen.

According to the invention, said gaseous fraction, in particular unconverted hydrogen originating from separation step c), is recycled to step a) of hydrotreating. Advantageously, said gaseous fraction is subjected to an optional step e) of removal of water before being recycled to step a) of hydrotreating. This step e) is carried out by any methods and techniques known to a person skilled in the art, such as drying, passing through a molecular sieve, decanting, etc. The gaseous fraction, advantageously originating from the optional step e), is recycled to step a) of hydrotreating, optionally at the same time as fresh hydrogen is added.

Step d) of fractionation of the liquid effluent originating from step c)

According to step d) of the method according to the invention, the liquid fraction originating from step c) undergoes a fractionation step, preferably in a distillation train that incorporates atmospheric distillation and optionally vacuum distillation. Said step d) has the aim of separating the conversion products with boiling point less than 220° C., preferably less than 290° C., more preferably less than 370° C. and including in particular those formed during step b) of hydroisomerization/hydrocracking. Step d) also makes it possible to separate the residual fraction the initial boiling point of which is generally above at least 220° C., and preferably above or equal to at least 370° C. Among the conversion products originating from step c) and hydroisomerized, besides the light gases, at least one gasoline (or naphtha) fraction and at least one fraction of middle distillate, kerosene and gas oil, are separated.

It may also be advantageous to recycle, to step a) or step b), at least some and preferably all of at least one of the kerosene or gas oil cuts thus obtained. The gas oil and kerosene cuts are preferably recovered separately or mixed, but the cut-off points can be adjusted as required.

Preferably, the residual fraction the initial boiling point of which is generally above at least 340° C., preferably above or equal to at least 370° C. is recycled to step a) or step b) of hydroisomerization/hydrocracking of the method according to the invention. According to another embodiment, said residual fraction can provide excellent bases for oils.

Description of FIG. 1

FIG. 1 shows a general diagram of the method according to the invention. According to FIG. 1, a feedstock 1 according to the invention is mixed with a hydrogen-rich stream 9 obtained from step c). The mixture thus constituted 2 is fed into a hydrotreating unit A. The liquid and gaseous effluent 3 originating from unit A is sent directly to the hydroisomerization/hydrocracking unit B.

The stream 4 originating from the hydroisomerization/hydrocracking unit B is separated by means known to a person skilled in the art in the separation unit C into a hydrogen-rich gaseous fraction 5 and a liquid fraction 6.

The liquid fraction 6 containing normal paraffins and iso-paraffins is sent to a fractionation section D, composed of atmospheric distillation and optionally vacuum distillation, to be separated into light gases ($C_1$-$C_4$) 14, naphtha 13, kerosene 12, gas oil 11 and residual fraction 10. In order to increase the yield of middle distillates, a part of the residual fraction can be recycled upstream of the hydrotreating unit A, stream 19, or of the hydroisomerization/hydrocracking unit, stream 20. A preferred means for improving the low-temperature properties of the gas oil cut is to recycle, in addition to the residual fraction 10, at least a part of the effluent 11 originating from the fractionation section D upstream of the hydrotreating unit A, stream 15, or of the hydroisomerization/hydrocracking unit B, stream 16. Similarly, the recycling of at least a part of the kerosene fraction 12 upstream of the hydrotreating unit A, stream 17, or of the hydroisomerization/ hydrocracking unit B, stream 18, allows considerable improvement of the low-temperature properties of the kerosene cut.

The gaseous fraction 5 originating from the separation unit C is hydrogen-rich and also contains the oxygenated compounds, such as carbon monoxide, carbon dioxide and water.

Optionally, the gaseous fraction 5 can pass through a unit for removing water E in order to reduce the quantity of water.

The gaseous fraction 7 originating from the optional unit for removing water E is recycled upstream of the hydrotreating unit A. If necessary, a supplement of hydrogen 8, fresh or obtained from conventional processes such as steam reforming, catalytic reforming etc., can be injected in a mixture with the hydrogen 7 obtained from step c) and advantageously after undergoing step e) for removal of water. The gaseous fraction 9 advantageously originating from the mixture of fresh hydrogen 8 and the recycled gaseous fraction 7 is recycled to the hydrotreating unit A.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 12/01.075, filed Apr. 12, 2012 are incorporated by reference herein.

EXAMPLES

Example 1

Effect of the Presence of the Oxygen Content in the Hydrogen for the Step of Hydrocracking/isomerization Hydrocracking of a feedstock originating from Fischer-Tropsch synthesis is carried out on a cobalt catalyst C2. The characteristics of the feedstock are given in Table 1 below:

TABLE 1

| Characteristics of the feedstock | | |
|---|---|---|
| density at 15° C. | 0.797 | g/cc |
| sulphur | <detection limit | ppmw |
| nitrogen | 7 | ppmw |
| oxygen | 0.3% | by weight |
| n-paraffins | 82% | by weight |
| i-paraffins | 6% | by weight |
| naphthenes | 0% | by weight |
| aromatics | 0% | by weight |
| olefins | 11% | by weight |
| simulated distillation | | |
| 5 | 175° C. | |
| 20 | 228° C. | |
| 50 | 346° C. | |
| 70 | 424° C. | |
| 95 | 570° C. | |
| compounds 370° C.+ | 43% | by weight |

The hydrocracking catalyst C2 is prepared according to the following protocol.

Preparation of the Support

The silica-alumina powder is prepared according to the following synthesis protocol. The quantities of orthosilicic acid and of aluminium alcoholate are selected so as to have a composition of 70% by weight $Al_2O_3$ and 30% by weight $SiO_2$ in the final solid. The powder is dried and brought into contact with a quantity of aqueous solution such that the loss on ignition at 550° C. of the cake obtained is about 60% by weight. This cake is mixed and then extruded. The mixing is carried out in a Z-arm mixer. Extrusion is carried out by passing the paste through a die with openings with a diameter of 1.4 mm. The extrudates thus obtained are dried in a stove at 110° C. and then calcined under a flow of dry air (rate of increase 5° C./min). The calcination temperature is adjusted so as to obtain a specific surface area of 310 $m^2/g$.

Preparation of the Catalyst

The silica-alumina extrudates are then subjected to a step of dry impregnation with an aqueous solution of hexachloroplatinic acid $H_2PtCl_6$, left to mature in a water soaker for 24 hours at room temperature and then calcined for two hours under dry air in fluidized bed at 500° C. (rate of temperature increase 5° C./min). The content by weight of platinum in the final catalyst after calcination is 0.70%.

The characteristics of the catalyst thus prepared are as follows:

- a mean mesopore diameter of 6.5 nm,
- a pore volume of the pores the diameter of which is comprised between the average diameter as defined above reduced by 3 nm and the average diameter as defined above increased by 3 nm equal to 60% of the total pore volume,
- a total pore volume of 0.70 ml/g,
- a BET surface area of 310 $m^2/g$,
- a sodium content of 110±13 ppm by weight,
- a dispersion of the noble metal of 85%,
- a distribution coefficient of the noble metal equal to 0.92.

Hydrocracking Operating Conditions

Hydrocracking was carried out under the following conditions:

hourly space velocity HSV (volume of feedstock/volume of catalyst/hour)=
2 $h^{-1}$
total working pressure: 5 MPa
hydrogen/feedstock ratio: 300 normal litres/litre
temperature: 270° C.

In order to measure the effect of the oxygenated compounds on catalyst C2, the hydrogen used originates from a standard mixture obtained from Air Liquide containing:

700 ppmv (parts per million by volume) of oxygen
1400 ppmv of oxygen.

Said hydrogen streams do not undergo any purification step.

These results are compared with a test carried out with hydrogen having an oxygen content less than 50 ppmv, conducted under the same operating conditions. Table 2 shows the distribution by cut of the hydrocracked effluent as a function of the oxygen content in the hydrogen.

Analyses by gas chromatography make it possible to obtain the distribution of the various cuts in the hydrocracked effluent (Table 2):

$C_1$-$C_4$ cut: hydrocarbons with 1 to 4 carbon atoms inclusive
$C_5$-$C_9$ cut: hydrocarbons with 5 to 9 carbon atoms inclusive (naphtha cut)
$C_{10}$-$C_{14}$ cut: hydrocarbons with 10 to 14 carbon atoms inclusive (kerosene cut)

$C_{15}$-$C_{22}$ cut: hydrocarbons with 15 to 22 carbon atoms inclusive (gas oil cut)

$C_{22+}$ cut: hydrocarbons with more than 22 carbon atoms (370° C.+ cut).

TABLE 2

Distribution of cuts of the hydrocracked effluent (GC analysis) as a function of the oxygen content in the hydrogen.

| | content of atomic oxygen in the hydrogen, ppmv | | |
|---|---|---|---|
| | <50 | 700 | 1400 |
| $C_1$-$C_4$ cut, % by weight | 2.3 | 2.0 | 1.8 |
| $C_5$-$C_9$ cut, % by weight | 11.6 | 10.2 | 9.2 |
| $C_{10}$-$C_{14}$ cut, % by weight | 31.8 | 30.6 | 30.0 |
| $C_{15}$-$C_{22}$ cut, % by weight | 41.7 | 40.8 | 40.5 |
| $C_{22}{}^+$ cut, % by weight | 12.6 | 16.4 | 18.5 |

Comparison of the results shows that the presence of oxygen in the hydrogen has a negative impact on the performance of the hydrocracking and isomerization catalyst. Thus, the percentage of middle distillates ($C_{10}$-$C_{22}$ cut) present in the hydrocracked effluent is decreased when oxygen is present in the hydrogen since this percentage changes from 73.5% for a content of atomic oxygen less than 50 ppmv to 71.4% for a content equal to 700 ppmv and to 70.5% for a content equal to 1400 ppmv.

Example 2

Treatment of a Feedstock Originating from a Fischer-Tropsch Synthesis by the Method According to the Invention The feedstock treated by the method of the invention is an effluent originating from Fischer-Tropsch synthesis. The feedstock has the following characteristics shown in Table 3:

TABLE 3

Characteristics of the feedstock

| density at 15° C. | 0.784 g/cc |
|---|---|
| sulphur | 1.3 ppmw |
| nitrogen | 1.4 ppmw |
| oxygen | 0.8% by weight |
| n-paraffins | 77% by weight |
| i-paraffins | 3.5% by weight |
| naphthenes | 0.1% by weight |
| aromatics | 0.0% by weight |
| olefins | 15% by weight |
| simulated distillation | |
| 5 | 120° C. |
| 20 | 196° C. |
| 50 | 318° C. |
| 70 | 400° C. |
| 95 | 547° C. |
| compounds 370° C.+ | 37% by weight |

In order to study the influence of the steps of the method, analyses for characterization of the effluents are carried out at the outlet of the hydrotreating step of the method of the invention.

The hydrotreating catalyst C1 is of the NiMo type supported on an alumina-based support. This catalyst is marketed by AXENS under reference HR945.

After reduction of catalyst C1, the feedstock is injected in the presence of hydrogen into the hydrotreating section.

The operating conditions for hydrotreating are:
Pressure=6.5 MPa,
Temperature=335° C.
Hourly space velocity (LHSV)=1 $h^{-1}$
$H_2$/HC=600 L/L The characteristics of the effluent originating from step a) are shown in Table 4:

TABLE 4

Characteristics of the effluent originating from step a)

| density at 15° C. | 0.785 g/cc |
|---|---|
| sulphur | <detection limit ppmw |
| nitrogen | <detection limit ppmw |
| oxygen | 0% by weight |
| n-paraffins | 95% by weight |
| i-paraffins | 5% by weight |
| naphthenes | 0% by weight |
| aromatics | 0% by weight |
| olefins | 0% by weight |
| simulated distillation | |
| 5 | 126° C. |
| 20 | 198° C. |
| 50 | 320° C. |
| 70 | 403° C. |
| 95 | 525° C. |
| compounds 370° C.+ | 37% by weight |

The hydrotreating catalyst has no cracking activity. The olefins and the oxygenated compounds measured by chromatography are completely decomposed. The decomposition of the oxygenated compounds produces CO, $CO_2$ and water by the reactions of decarboxylation, decarbonylation and dehydration.

Analyses of the gas phase leaving step a) show a content of CO and $CO_2$<10 ppm by volume.

The method according to the invention makes it possible, in step a), to hydrotreat the feedstock by hydrogenation of the olefins and to decompose the oxygenated compounds. The compounds CO and $CO_2$, which are harmful to catalyst C2 as shown in example 1, are converted simultaneously by catalyst C1.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Method for producing middle distillates from a feedstock produced by Fischer-Tropsch synthesis and containing oxygenated compounds, said method comprising at least:
   a) a step of bringing the feedstock into contact with a hydrotreating catalyst which results in methanation of the CO and $CO_2$ which is contained in the feedstock or is produced from decomposition of the oxygenated compounds present in the feedstock, at a temperature between 320 and 450° C., at a pressure between 0.5 and 15 MPa, and introducing the hydrogen necessary for the reaction of hydrotreating and of methanation at a flow rate such that the hydrogen/feedstock volume ratio is between 100 and 3000 normal liters per liter, and at an hourly space velocity between 0.1 and $40^{-1}$, to obtain a liquid and gaseous effluent,
   b) a step of hydroisomerization/hydrocracking at least a part of the liquid and gaseous effluent originating from step a), in the presence of a hydroisomerization/hydrocracking catalyst, to obtain an effluent, c) a step of gas/liquid separation of the effluent originating from step b) into a gaseous fraction comprising predominantly hydrogen and a hydroisomerized/hydrocracked liquid fraction, d) a step of fractionation of the liquid fraction separated in step c) to obtain at least one fraction of middle distillate, in which the hydrogen used in step a) is, at least partly, obtained from the gaseous fraction separated in step c).

2. Method according to claim 1 in which said feedstock produced by Fischer-Tropsch synthesis comprises a content of n-paraffins greater than 60% by weight relative to the total weight of said feedstock, a content of oxygenated compounds less than 10% by weight, a content of unsaturated compounds less than 20% by weight and a content of iso-paraffins less than 10% by weight relative to the total weight of said feedstock.

3. Method according to claim 1 in which the catalyst used in step a) comprises at least one hydrogenating-dehydrogenating metal selected from the group comprising the metals of group VIB and of group VIII of the periodic table on a support.

4. Method according to claim 3 in which the catalyst used in step a) comprises at least one group VIII non-noble metal selected from nickel and cobalt in combination with at least one group VIB metal selected from molybdenum and tungsten, used alone or in a mixture.

5. Method according to claim 4 in which the support of the catalyst used in step a) is a support based on alumina.

6. Method according to claim 5 in which the support of the catalyst used in step a) is a support based on alumina containing a group VIII metal selected from nickel or cobalt.

7. Method according to claim 1 in which the catalyst used in step a) has a BET specific surface area from 100 to 300 $m^2/g$, a mean mesopore diameter between 6 and 20 nm, a pore volume of the pores having a diameter between the mean mesopore diameter reduced by 3 nm and the mean mesopore diameter increased by 3 nm of greater than 20% of the total pore volume, and a total pore volume between 0.1 and 1 ml/g.

8. Method according to claim 1 in which the catalyst used in step a) is used in reduced form.

9. Method according to claim 1 in which step a) is carried out at a temperature between 320 and 400° C., at a pressure between 1 and 10 MPa, with a hydrogen flow rate such that the hydrogen/feedstock volume ratio is between 100 and 2000 normal liters per liter and at an hourly space velocity between 0.2 and 30 $h^{-1}$.

10. Method according to claim 1 in which step b) is implemented on all of the effluent originating from step a).

11. Method according to claim 1 in which step b) is carried out at a temperature between 250 and 450° C., at a pressure between 0.2 and 15 MPa, at a space velocity comprised between 0.1 $h^{-1}$ and 10 $h^{-1}$, and at a hydrogen rate between 100 and 2000 normal liters of hydrogen per liter of feedstock per hour.

12. Method according to claim 1 in which said gaseous fraction separated in step c) is subjected to a step e) of removal of water before being recycled to step a) of hydrotreating.

13. Method according to claim 12 in which said gaseous fraction separated in step c) is recycled to step a) of hydrotreating at the same time as fresh hydrogen is supplied.

* * * * *